(12) United States Patent
Rice et al.

(10) Patent No.: US 11,937,999 B2
(45) Date of Patent: Mar. 26, 2024

(54) METHOD AND SYSTEM FOR PROVIDING ACTIVE TISSUE SITE DEBRIDEMENT

(71) Applicant: KCI Licensing, Inc., San Antonio, TX (US)

(72) Inventors: Justin R. Rice, San Antonio, TX (US); Christopher A. Carroll, San Antonio, TX (US); Lydia Galarza, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 739 days.

(21) Appl. No.: 17/056,956

(22) PCT Filed: May 23, 2019

(86) PCT No.: PCT/US2019/033758
§ 371 (c)(1),
(2) Date: Nov. 19, 2020

(87) PCT Pub. No.: WO2019/226900
PCT Pub. Date: Nov. 28, 2019

(65) Prior Publication Data
US 2021/0205142 A1    Jul. 8, 2021

Related U.S. Application Data

(60) Provisional application No. 62/676,588, filed on May 25, 2018.

(51) Int. Cl.
*A61F 13/00*    (2006.01)
*A61B 17/00*    (2006.01)
(Continued)

(52) U.S. Cl.
CPC ........ *A61F 13/00063* (2013.01); *A61B 17/00* (2013.01); *A61F 13/01029* (2024.01);
(Continued)

(58) Field of Classification Search
None
See application file for complete search history.

(56) References Cited

U.S. PATENT DOCUMENTS

| 1,355,846 | A | 10/1920 | Rannells |
| 2,547,758 | A | 4/1951 | Keeling |
(Continued)

FOREIGN PATENT DOCUMENTS

| AU | 550575 B2 | 3/1986 |
| AU | 745271 B2 | 3/2002 |
(Continued)

OTHER PUBLICATIONS

International Search Report & Written Opinion in International Application No. PCT/US2019/033758, dated Oct. 21, 2019.
(Continued)

*Primary Examiner* — Kim M Lewis

(57) ABSTRACT

A wound debridement system includes a wound dressing having an active layer and a wound interface layer. The active layer is formed from one or more transmission layers that are arranged about a central post. Activation of the transmission layers is configured to cause the movement of the wound interface layer relative to a tissue site to which the wound dressing is applied. A drive unit is operably attached to the central post. The drive unit is configured to generate and transfer a vibrational energy and/or a rotational movement to the transmission layer(s) via the central post. The resultant vibration and/or rotation of the transmission layer(s) is imparted onto the wound interface layer, thereby effectuating the desired movement of the wound interface layer relative to the tissue site, which allows for the debridement of debris that may be located at the tissue site.

20 Claims, 4 Drawing Sheets

(51) Int. Cl.
   *A61F 13/01*      (2024.01)
   *A61F 13/05*      (2024.01)
   *A61M 1/00*       (2006.01)
   *A61B 17/32*      (2006.01)

(52) U.S. Cl.
   CPC ........ *A61F 13/01034* (2024.01); *A61F 13/05* (2024.01); *A61M 1/915* (2021.05); *A61M 1/92* (2021.05); *A61B 2017/00761* (2013.01); *A61B 2017/320008* (2013.01); *A61M 2205/103* (2013.01); *A61M 2205/106* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 8,672,903 | B2* | 3/2014 | Hunt ............... A61L 15/26 604/289 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2013/0165821 | A1* | 6/2013 | Freedman ............ A61M 1/77 604/20 |
| 2015/0320603 | A1* | 11/2015 | Locke ............ A61B 17/3205 604/543 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3616669 A1 * | 3/2020 ............ A61B 18/04 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| | | |
|---|---|---|
| WO | 99/13793 A1 | 3/1999 |
| WO | WO-2013/066694 A2 | 5/2013 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

METHOD AND SYSTEM FOR PROVIDING ACTIVE TISSUE SITE DEBRIDEMENT

CROSS-REFERENCE TO RELATED APPLICATIONS

This Application claims the benefit of priority to international patent application number PCT/US2019/033758, filed on May 23, 2019, which claims the benefit of priority to U.S. Provisional Application No. 62/676,588, filed on May 25, 2018, the complete disclosures of which are hereby incorporated herein by reference in their entireties.

BACKGROUND

The present disclosure relates generally to tissue treatment systems, and more particularly, but without limitation, to a wound debridement system for active disruption and/or debridement of non-viable tissue at a tissue site without continual user intervention.

During treatment of a tissue site, such as, e.g. a wound site, debris may develop on or in the tissue site. In various embodiments, the debris may include biofilms, necrotic tissue, foreign bodies, eschar, lacerated tissue, devitalized tissue, contaminated tissue, damaged tissue, infected tissue, exudate, highly viscous exudate, fibrinous slough and/or other material. The debris may cover all or a portion of the tissue site.

The presence of debris in, on, or surrounding a tissue site may cause numerous problems. For example, debris that covers the tissue site may impair healing of the tissue site. Debris can also lower the effectiveness of beneficial tissue site treatments by preventing the treatments from reaching the tissue site. The presence of debris may also increase healing times and the risk of a more serious infection. Accordingly, in various embodiments, it may be desirable to disrupt the debris at a tissue site in order to promote healing of the tissue site.

SUMMARY

One implementation of the present disclosure is an active debridement wound dressing including a wound interface layer and an active layer. The wound interface layer is configured to contact a wound and mechanically debride the wound when the wound interface layer moves relative to the wound. The active layer is coupled to the wound interface layer and includes a transmission layer extending radially outwards relative to a central post. The transmission layer is configured to vibrate when activated so as to move the wound interface layer relative to the wound and mechanically debride the wound.

In some embodiments, the transmission layer is formed from a plurality of arm members. In some embodiments, the plurality of arm members form an interconnected, interrupted planar structure.

In some embodiments, the wound interface layer is formed from a foam-like material. A plurality of through-holes extend through the wound interface layer. The plurality of through-holes are distinct from pores which define the foam-like material from which the wound interface is formed. In some embodiments, the active debridement wound dressing includes an absorbent layer.

In some embodiments, the transmission layer is positioned on top of a top surface of the wound interface layer and below a lower surface of the absorbent layer. In some embodiments, the transmission layer is at least partially embedded within the wound interface layer. In some embodiments, the transmission layer is entirely embedded within the wound interface layer.

In some embodiments, the arm members are formed from a semi-rigid material. In some embodiments, the active layer includes a plurality of vertically spaced transmission layers. In some embodiments, the transmission layer is fixedly attached to the central post. In some embodiments, the transmission layer is movably attached to the central post, such that the transmission layer may be rotated relative to the central post.

In some embodiments, the transmission layer is configured to vibrate in response to a vibrational energy being transmitted to the transmission layer by the central post.

In some embodiments, the active debridement wound dressing includes a drive unit configured to generate a vibrational energy operably attached to the central post. A control unit may be coupled to the drive unit. The control unit is configured to activate the drive unit to generate a vibrational energy that is transmitted to the transmission layer.

In some embodiments, the active debridement wound dressing includes a drape layer sealable to a patient's skin surrounding the wound. The drape layer is configured to maintain the wound dressing at a desired treatment area.

In some embodiments, the active debridement wound dressing includes a semi-rigid support layer positioned between the drape layer and the wound dressing. The support layer is configured to prevent the wound dressing from sticking to the drape layer and to prevent the wound dressing from being unintentionally displaced from the desired treatment area in response to a vibrational energy being applied to the wound dressing.

One implementation of the present disclosure is an active debridement wound dressing including a wound interface layer and an active layer. The wound interface layer is configured to contact a wound and mechanically debride the wound when the wound interface layer moves relative to the wound. The active layer is coupled to the wound interface layer and includes a transmission layer extending radially outwards relative to a central post. The transmission layer is configured to rotate when activated so as to move the wound interface layer relative to the wound and mechanically debride the wound.

In some embodiments, the transmission layer is formed from a plurality of arm members. In some embodiments, the plurality of arm members form an interconnected, interrupted planar structure.

In some embodiments, the wound interface layer is formed from a foam-like material. A plurality of through-holes extend through the wound interface layer. The plurality of through-holes are distinct from pores which define the foam-like material from which the wound interface is formed. In some embodiments, the active debridement wound dressing includes an absorbent layer.

In some embodiments, the transmission layer is positioned on top of a top surface of the wound interface layer and below a lower surface of the absorbent layer. In some embodiments, the transmission layer is at least partially embedded within the wound interface layer. In some embodiments, the transmission layer is entirely embedded within the wound interface layer.

In some embodiments, the arm members are formed from a semi-rigid material. In some embodiments, the active layer includes a plurality of vertically spaced transmission layers. In some embodiments, the transmission layer is fixedly attached to the central post. In some embodiments, the transmission layer is movably attached to the central post, such that the transmission layer may be rotated relative to the central post.

In some embodiments, the transmission layer is configured to rotate in response to a rotational movement being transmitted to the transmission layer by the central post.

In some embodiments, the active debridement wound dressing includes a drive unit configured to generate a rotational movement operably attached to the central post. A control unit may be coupled to the drive unit. The control unit is configured to activate the drive unit to generate a rotational movement that is transmitted to the transmission layer.

In some embodiments, the active debridement wound dressing includes a drape layer sealable to a patient's skin surrounding the wound. The drape layer is configured to maintain the wound dressing at a desired treatment area.

In some embodiments, the active debridement wound dressing includes a semi-rigid support layer positioned between the drape layer and the wound dressing. The support layer is configured to prevent the wound dressing from sticking to the wound dressing and to prevent the wound dressing from being unintentionally displaced from the desired treatment area in response to a rotational movement being applied to the wound dressing.

In some embodiments, the rotational movement that is transmitted to the transmission layer is configured to rotate the transmission layer relative to the central post and is also configured to rotate the central post relative to the wound. In some embodiments, the central post is configured to remain stationary relative to the wound when rotational movement is transmitted to the central post.

In some embodiments, rotational movement that is transmitted to the central post is configured to rotate the central post relative to the wound while the transmission layer remains stationary relative to the central post.

One implementation of the present disclosure is an active debridement wound therapy system including a wound interface layer, an active layer, and a therapy unit. The wound interface layer is configured to contact a wound and mechanically debride the wound when the wound interface layer moves relative to the wound. The active layer is coupled to the wound interface layer and includes a transmission layer extending radially outwards relative to a central post. The transmission layer is configured to vibrate when activated so as to move the wound interface layer relative to the wound and mechanically debride the wound. The therapy unit is separate from the wound dressing and is configured to generate and apply a vibrational energy to the active layer.

One implementation of the present disclosure is an active debridement wound therapy system including a wound interface layer, an active layer, and a therapy unit. The wound interface layer is configured to contact a wound and mechanically debride the wound when the wound interface layer moves relative to the wound. The active layer is coupled to the wound interface layer and includes a transmission layer extending radially outwards relative to a central post. The transmission layer is configured to rotate when activated so as to move the wound interface layer relative to the wound and mechanically debride the wound. The therapy unit is separate from the wound dressing and is configured to generate and apply a rotational movement to the active layer.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Referring to FIGS. 1-4, various embodiments of a wound debridement system 1 configured to disrupt areas of debris 7 at a tissue site 5, such as, e.g. a wound site, are shown. The wound debridement system 1 is configured to provide continued, active and/or intermittent mechanical debridement of debris 7 at the tissue site 5 without requiring any additional user skill or effort to operate the wound debridement system 1 than would be required to apply and activate an existing negative pressure wound therapy ("NPWT") system, such as e.g. a V.A.C® therapy unit as available from Kinetic Concepts, Inc. (KCI) of San Antonio, Tex.

Figure 1:
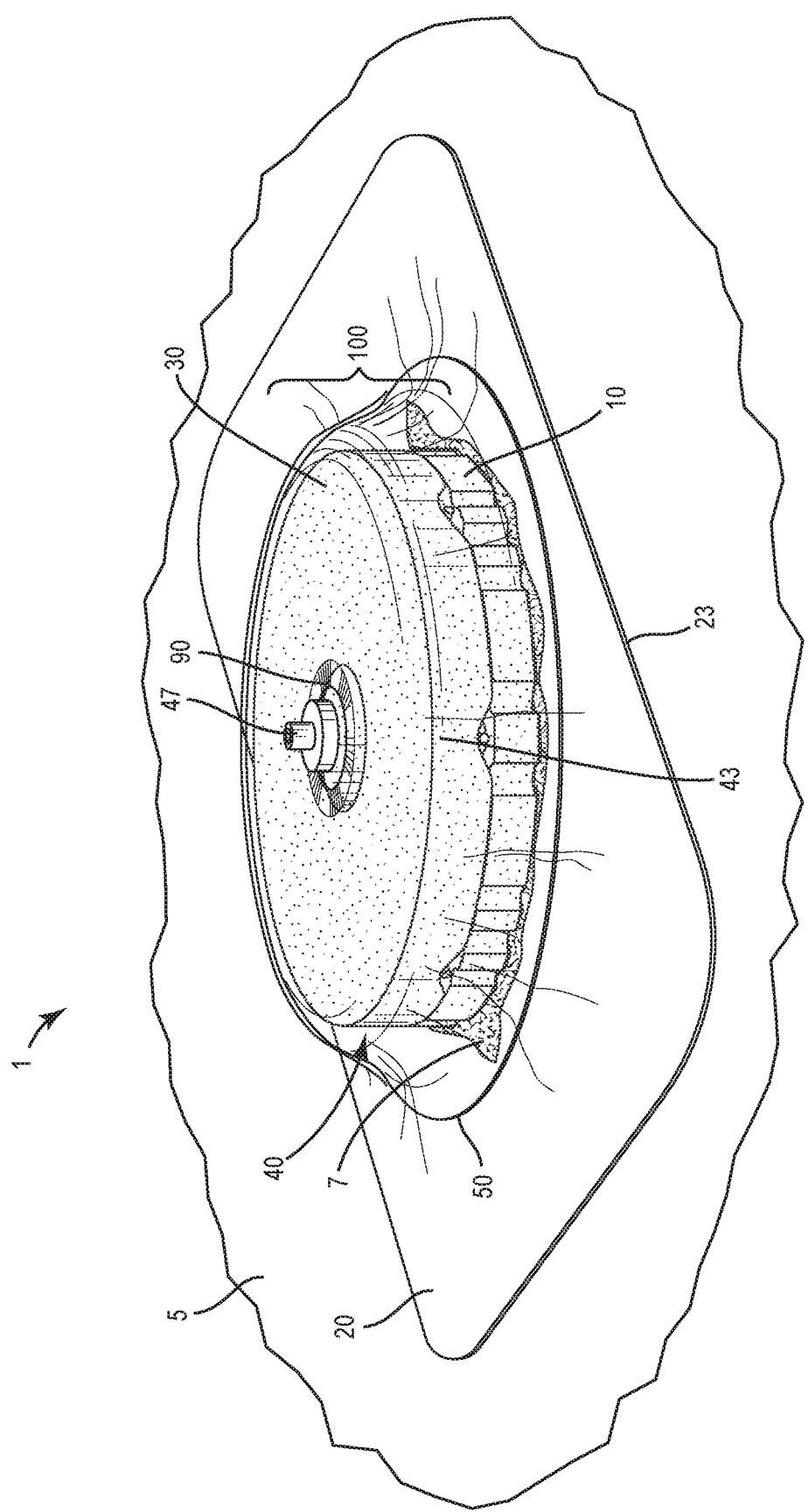
FIG. 1 is a top perspective view of an active wound debridement system applied to a tissue site, according to an exemplary embodiment.
Figure 3A:
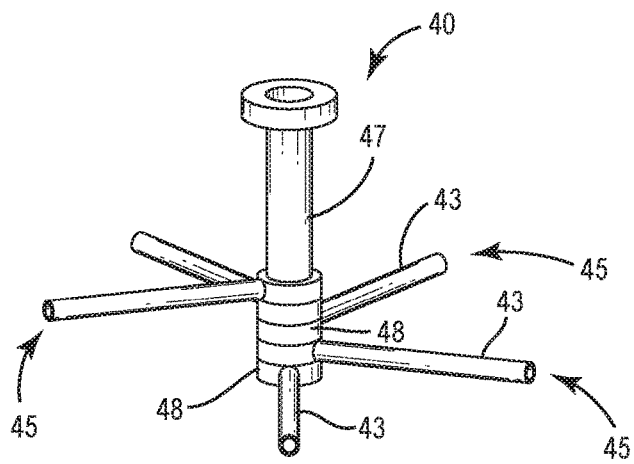
FIG. 3A illustrates an active layer according to an exemplary embodiment.
Figure 3B:
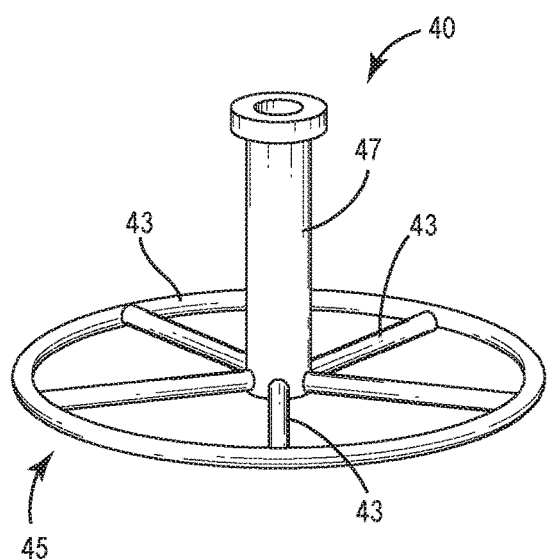
FIG. 3B illustrates an active layer according to an exemplary embodiment.
Figure 3C:
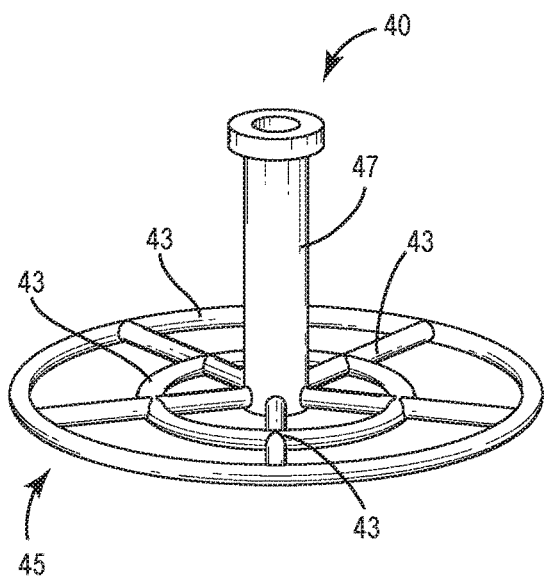
FIG. 3C illustrates an active layer according to an exemplary embodiment.
Figure 3D:
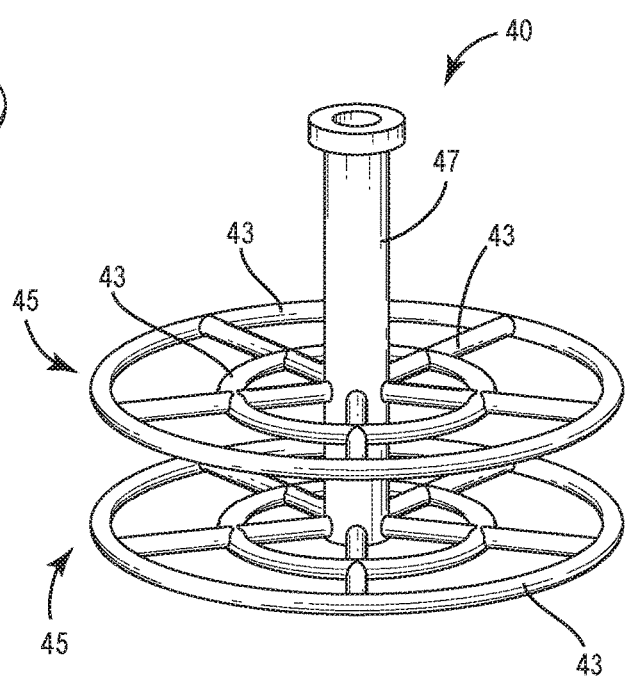
FIG. 3D illustrates an active layer according to an exemplary embodiment.
Figure 4A:
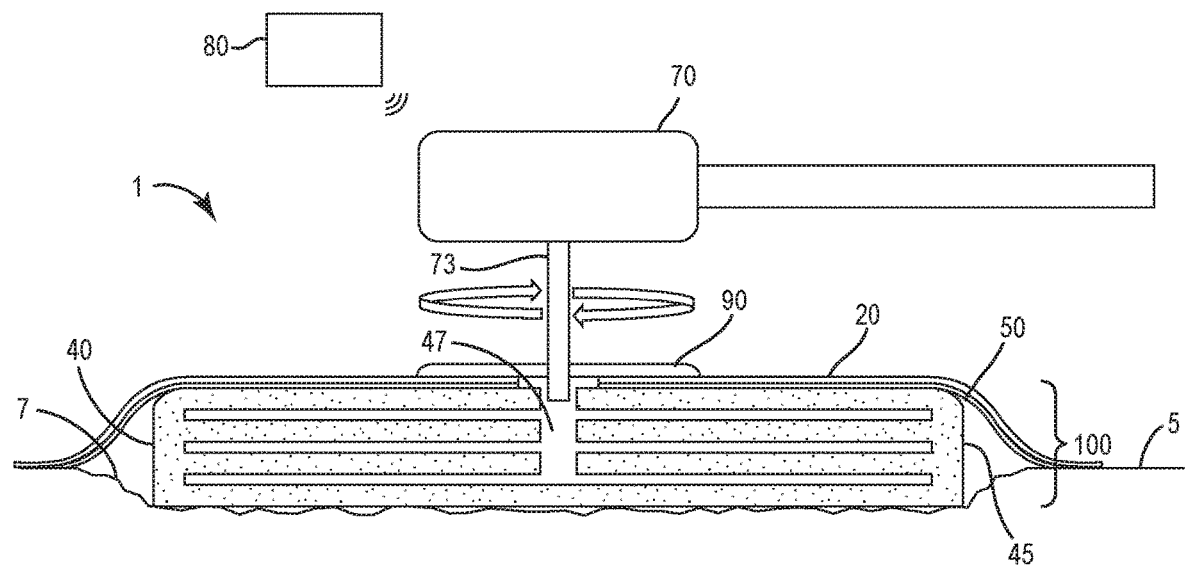
FIG. 4A is a cross-sectional view of an active wound debridement system configured to impart a rotational movement to a wound dressing according to an exemplary embodiment.
Figure 4B:
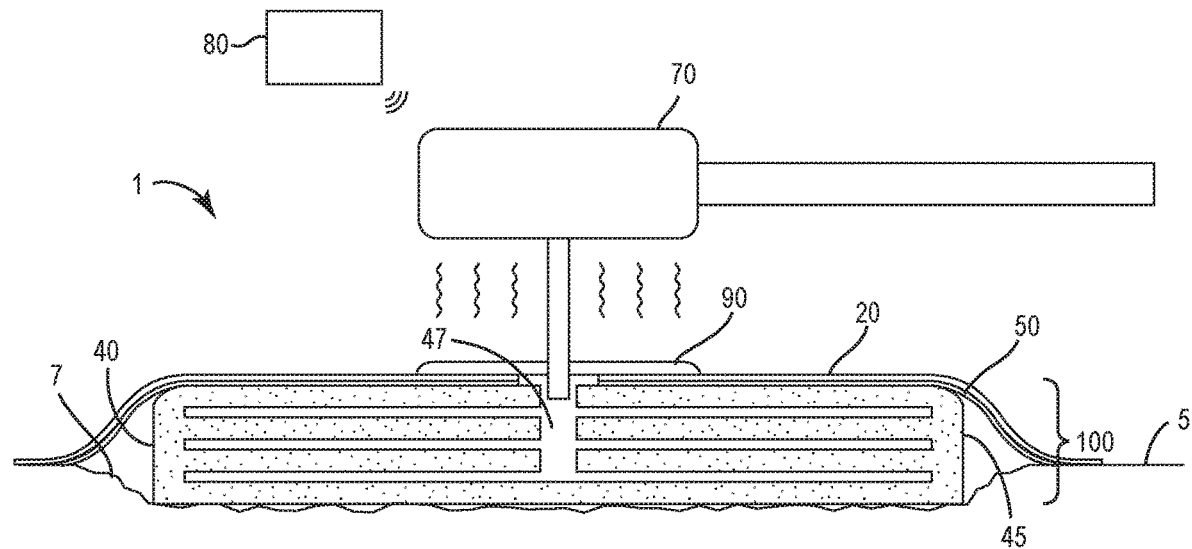
FIG. 4B is a cross-sectional view of an active wound debridement system configured to impart a vibrational energy to a wound dressing according to an exemplary embodiment.

As shown in FIGS. 1, 4A and 4B, the wound debridement system 1 generally comprises a wound dressing 100, a support layer 50 configured to allow the wound dressing 100 to vibrate and/or oscillate (i.e. rotate) freely under a drape layer 20, a drape layer 20 that is configured to position the wound dressing 100 at a desired tissue site 5, a drive unit 70 adapted to activate an active layer 40 (see, e.g. FIGS. 2 and 3A-3D), and a control unit 80 configured to control the activation of the active layer 40 by the drive unit 70.

During operation of the wound debridement system 1, the wound dressing 100 is positioned on or within a desired tissue site 5. Once positioned, the support layer 50 is positioned atop the wound dressing 100, and the support layer 50 and the wound dressing 100 are secured to the patient's skin using the drape layer 20. In some embodiments, the drape layer 20 may be applied to the patient's skin so as to form a sealed, substantially fluid-tight treatment space surrounding the tissue site 5.

The control unit 80 may be operated to control the activation of the active layer 40 by the drive unit 70. The activation of the active layer 40 delivers a gentle vibrational energy and/or oscillatory movement to the wound interface layer 10 (see, e.g. FIGS. 1 and 2) so as to effectuate a slight displacement of the wound interface layer 10 relative to the tissue site 5.

The movement of the wound interface layer 10 relative to the tissue site 5 acts to mechanically disrupt and debride debris 7 located at the tissue site 5, and may also help minimize the ingrowth of debris into the wound dressing 100 during treatment of a tissue site 5 using the wound dressing 100. Additionally, in some embodiments, the gentle vibration and/or oscillatory motion imparted onto the tissue site 5 may induce an acute inflammatory response that may promote in healing of the tissue site 5.

The impact of the operation of the wound debridement system 1 on the tissue site 5 may depend on any number of factors, including the timing of the debridement, the tissue site 5 etiology, and/or any additional treatments that are applied to the tissue site 5. For example, repeated debridement using the wound debridement system 1 early in the therapy regimen of a tissue site 5 may act to disrupt existing debris at the tissue site 5. The repeated, continued debridement using the wound debridement system 1 during the therapy regimen of a tissue site 5 may be used to disrupt and/or inhibit the formation/accumulation of new debris 7 (e.g. biofilm).

In some embodiments, treatment of the tissue site 5 may be enhanced by utilizing the wound debridement system 1 in conjunction with an additional therapeutic treatment system (such as, e.g., a negative pressure wound therapy ("NPWT") and/or instillation therapy system). For example, in some embodiments, the wound debridement system 1 may be used to apply vibrations and/or oscillations from the drive unit 70 to the wound dressing 100 and tissue site 5 to disrupt and more easily solubilize debris 7 to enhance the effectiveness of NPWT and/or instillation therapy. Similarly, utilizing an instillation therapy treatment system to, e.g., apply pain management medication (e.g. topical lidocaine) and/or a solubilizing solution to the tissue site 5 during debridement may help to disrupt areas of stubborn debris 7 at the tissue site 5.

The wound debridement system 1 may be used to perform tissue site 5 debridement according to any number of different protocols. In some embodiments, operation of the wound debridement system 1 may be used with aggressive/fast debridement protocols, in which the wound debridement system 1 is operated for short periods of time over a treatment period, and in which the debridement may optionally be performed prior to, during, and/or following the delivery of a topical pain management medication to the tissue site 5.

In other embodiments, the wound debridement system 1 may be operated intermittently at a low-medium intensity one or more times per day, or may be operated continuously at low intensity over the span of the duration of a tissue treatment protocol so as to maintain the tissue site 5 free of debris during the tissue treatment. In yet other embodiments, the wound debridement system 1 may be operated in the hours/minutes immediately prior to the removal of the wound dressing 100 from the tissue site 5. In such embodiments, the wound debridement system 1 may be operated at a high energy for a prolonged duration, e.g. one hour prior to the removal of the wound dressing 100, so as to create a maximal disruption of debris, thereby facilitating removal of the wound dressing 100 (by disrupting any debris ingrown into the wound dressing 100) and/or by minimizing or negating the need for bed-side debridement by a medical practitioner prior to the application of a new wound dressing 100 to the tissue site 5.

Wound Dressing

In general, among other possible layers, the wound dressing 100 includes a wound interface layer 10 (see, e.g. FIGS. 1 and 2) configured to provide mechanical movement which disrupts debris 7 at a tissue site 5 and an active layer 40 configured to drive the movement of the wound interface layer 10. An absorbent layer 30 may optionally also be incorporated into the wound dressing 100.

The active layer 40 may be arranged relative to the wound interface layer 10 according to various embodiments. In some embodiments, such as, e.g. illustrated in FIGS. 4A and 4B, the transmission layer(s) 45 (described below) of the active layer 40 may be embedded within the wound interface layer 10. In other embodiments, such as, e.g. illustrated in FIGS. 1 and 2, the transmission layers 45 of the active layer 40 may be attached atop the wound interface layer 10.

In embodiments in which an absorbent layer 30 is included, the active layer 40 that is positioned atop the wound interface layer 10 may optionally be embedded in the absorbent layer 30, or the active layer 40 may be positioned in between the wound interface layer 10 and the absorbent layer 30. In other embodiments in which an absorbent layer 30 is included, the active layer 40 may be positioned atop both the wound interface layer 10 and the absorbent layer 30. Also, it is to be understood that in yet other embodiments, the wound dressing 100 may be formed without an active layer 40, with the active layer 40 instead being positioned atop the support layer 50 and/or atop the drape layer 20.

While the wound interface layer 10 and the absorbent layer 30 of the wound dressing 100 will typically be disposable, according to various embodiments, the active layer 40 may be capable of being reused with a new wound interface layer 10 and optional absorbent layer 30. In embodiments in which the active layer 40 is intended to be reusable, the active layer 40 may advantageously be incorporated into the wound dressing 100 on top of the wound interface layer 10 (and below the absorbent layer 30, if included) as opposed to being embedded, so as to facilitate the removal and reuse of the active layer 40. Additionally, by configuring the active layer 40 to be capable of being incorporated into the wound dressing 100 atop the wound interface layer 10, existing wound dressings formed without an active layer 40 may be retrofitted to include the active layer 40.

The wound dressing 100 may be substantially planar or may be contoured for application to body surfaces having high curvature. For example, the wound dressing 100 may have a substantially convex or concave shape, or other customizable topography to adhere to wounds located on areas such as the knee or elbow.

The size of wound dressing 100 can vary depending on the size of the tissue site 5 to be treated. For example, it is contemplated that the size of wound dressing 100 can be within a range of approximately 3 cm$^2$ to approximately 150 cm$^2$, and more preferably within a range of approximately 10 cm$^2$ to approximately 50 cm$^2$. However, other shapes and sizes of wound dressing 100 are also possible depending on intended use.

i. Wound Interface Layer

The wound interface layer 10 is adapted to contact a tissue site 5 along a lower, wound-facing surface 11 of the wound interface layer 10 to mechanically debride debris 7 at the tissue site 5 upon vertical, lateral and/or longitudinal movement of the wound interface layer 10 relative to the tissue site 5. Although the wound interface layer 10 is shown as having a generally round shape, the wound interface layer 10 may be formed having any number of, and combination of, sizes, shapes, and/or thicknesses depending on a variety of factors, such as, e.g. the type of treatment being implemented or the nature and size of the tissue site 5 being treated, etc.

Additionally, the size and shape of the wound interface layer 10 may be selected to accommodate the type of tissue site 5 being treated and the degree of contact (e.g. full or partial contact) desired between the tissue site 5 and the wound interface layer 10. For example, if the tissue site 5 is a wound, the shape, size and thickness of the wound interface layer 10 may vary depending on whether the wound interface layer 10 is intended to partially or completely fill the wound, or if the wound interface layer 10 is intended to only be placed over the wound. If the wound interface layer 10 is intended to partially or completely fill the wound, the size and shape of the wound interface layer 10 may be adapted to the contours of the wound. In embodiments in which the wound interface layer 10 is configured to fill the wound, the wound interface layer 10 may optionally be cut to a size corresponding generally to the size and shape of the wound which the wound interface layer 10 is intended to treat.

Any number of bio-compatible materials may be used to construct the wound interface layer 10. A non-limiting, non-exhaustive list of the various materials that may be used to form the wound interface layer 10 may include: bioresorbable materials; materials configured to serve as a scaffold for new cell-growth, such as, e.g. calcium phosphate, collagen, PLA/PGA, coral hydroxy apatites, carbonates, or processed allograft materials; thermoplastic elastomers; 3D textiles, also referred to as a spacer fabric, such as the 3D textiles produced by Heathcoat Fabrics, Ltd., Baltex, and Mueller Textil Group; foam, such as e.g. GranuFoam®, V.A.C. VeraFlo® foam, or V.A.C. WhiteFoam®, each available from Kinetic Concepts, Inc. of San Antonio, Texas; etc.

According to various embodiments, the materials used to form the wound interface layer 10, the properties of the wound-facing surface 11 and/or the configuration and structure of the wound-facing surface 11 may be selected to enhance the ability of the wound interface layer 10 to disrupt debris 7 at the tissue site 5. For example, in some embodiments, the wound-facing surface 11 may be formed of an abrasive material. In other embodiments, the wound-facing surface 11 may be defined by a textured surface having an uneven, coarse, or jagged profile that can induce strains and stresses at the tissue site 5. In such embodiments, the wound-facing layer may be formed of an abrasive or non-abrasive material. In yet other embodiments, the wound interface layer 10 may be formed of an abrasive or non-abrasive compressible material, with the compression of the compressible material being adapted to increase the amount by which the wound-facing surface 11 is translated or oscillated laterally and/or longitudinally relative to the tissue site 5 during treatment.

In various embodiments, the wound-facing surface 11 of wound interface layer 10 may be formed having a generally solid, continuous, uninterrupted surface. In other embodiments, particularly when the wound debridement system 1 is used in conjunction with a NPWT treatment or other treatment in which negative pressure is applied to the tissue site 5, the ability of the wound interface layer 10 to disrupt debris 7 at the tissue site 5 may be enhanced via the selective removal of areas or portions of the wound-facing surface 11.

Figure 2:
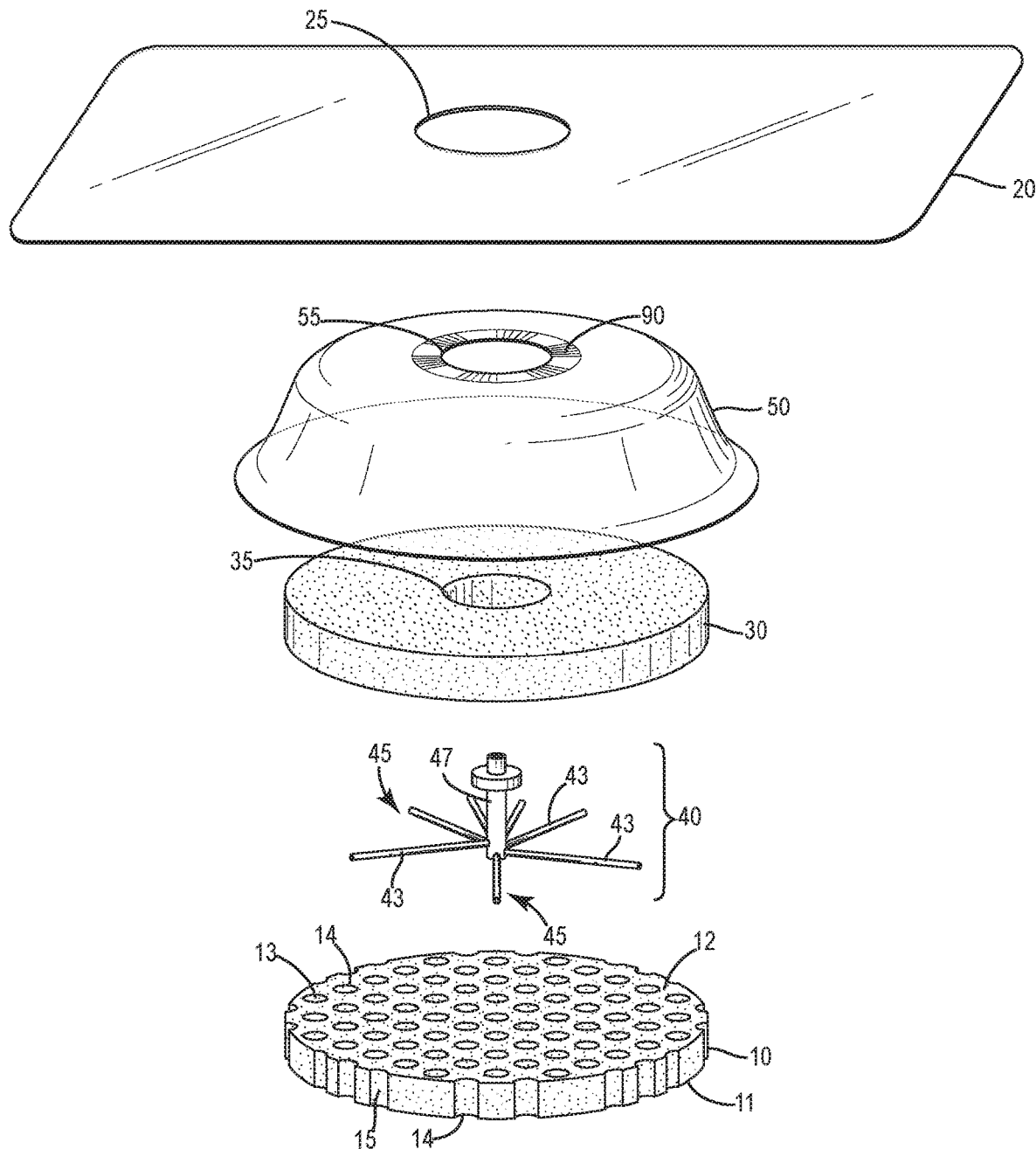
FIG. 2 is an exploded top perspective view of a wound dressing according to an exemplary embodiment.

For example, as illustrated in FIGS. 1 and 2, in one embodiment, the wound interface layer 10 may be constructed with a plurality through-holes 13 extending entirely or partially through the wound interface layer 10 from the wound-facing surface 11 to an upper surface 12 of the wound interface layer 10.

The plurality of through-holes 13 may have any number of different shapes and may be arranged about the wound interface layer 10 in any desired manner to define any number of different uniform or non-uniform patterns (such as, e.g., perforated, grid-like, honeycombs, etc.) extending entirely or partially from the wound-facing surface 11 to the upper surface 12 of the wound interface layer 10.

The dimensions of the through-holes 13 may be varied as desired. While in some embodiments each of the through-holes 13 may have identical dimensions, in other embodiments the through-holes 13 may be formed having varied dimensions. Regardless of the dimensions selected for the through-holes 13, in embodiments in which the wound interface layer 10 is formed from a foam-like or other porous material, it is to be understood that the through-holes 13 do not include the pores of the material forming the wound interface layer 10, but rather are discrete perforations formed through the material forming the wound interface layer 10.

The through-holes 13 may be arranged about the wound interface layer 10 in any number of desired arrangements or patterns, including a random arrangement of the through-holes 13 about the wound interface layer 10. As illustrated in FIG. 2, in some embodiments, the through-holes 13 may be arranged linearly, with adjacent rows of through-holes 13 optionally being offset from one another.

As shown in FIG. 2, in some embodiments, the through-holes 13 may have a circular shape. In other embodiments, the through-holes 13 may be formed having any number of other shapes, or any combination of different shapes, including, e.g. hexagonal, ovoid, or triangular shapes. When contracted, through-holes 13 having different cross-sectional shapes may generate and distribute concentrated stresses in different dimensions, and may accordingly influence disruption of debris 7 in different ways. As such, in various embodiments the cross-sectional shape of the through-holes 13 may be based on the tissue site 5 being treated and/or the degree of abrasion that may be desired at the tissue site 5.

Regardless of the shape, size, arrangement, or degree to which the through-holes 13 extend through the wound interface layer 10, the through-holes 13 formed in the wound interface layer 10 define void spaces in the wound-facing surface 11. In response to the wound interface layer 10 being compressed (e.g. as a result of activation of the active layer 40 and/or upon application of negative pressure in embodiments in which the wound debridement system 1 is used in conjunction with a NPWT device), the voids provide spaces into which the wound-facing surface 11 is laterally and/or longitudinally collapsed. As the wound-facing surface 11 is compressed from its initial, relaxed configuration into the spaces defined by the voids, the lateral and/or longitudinal translation of the wound-facing surface 11 relative to the tissue site 5 concentrates a shear force on the tissue site 5 that allows for the disruption of the debris 7 at the tissue site 5.

The disruption of the debris 7 at the tissue site 5 may also be augmented by the localization of forces along the edges 14 of the through-holes 13 during compression of the wound interface layer 10, which may result in the edges 14 acting as cutting surfaces that disrupt debris 7 at the tissue site 5. Additionally, in some embodiments, as a result of the compression of the wound interface layer 10, debris 7 may become trapped within the voids as the through-holes 13 collapse. Forces concentrated by the inner vertical surfaces 15 of the walls of the through-holes 13 on this trapped debris 7 may act to provide additional disruption of the debris 7 at the tissue site 5.

In some embodiments (not shown), the selective removal of areas or portions of the wound interface layer 10 may be provided in the form of the wound interface layer 10 being formed of a plurality of discrete or connected segments. In an initial configuration—prior to the compression of the wound interface layer 10—the segments may be arranged and spaced relative to one another with voids separating adjacent segments, such that the wound-facing surface 11 of the wound interface layer 10 is defined by a non-solid, interrupted surface. The segments may be arranged relative to one another such that, upon compression of the wound interface layer 10 (e.g. in response to a negative pressure applied via a NPWT system used in conjunction with the wound debridement system 1), the segments collapse inwards to form a substantially solid, compact surface defined by the inter-fitted arrangement of adjacent segments with one another.

The effect of the contraction of the segments of wound interface layer 10 is similar to the effect of the contraction and collapse of through-holes 13 of wound interface layer 10 embodiments such as that illustrated in, e.g. FIG. 2. In particular, the translation of the segments relative to the tissue site 5 concentrates a shear force on the tissue site 5 as the segments are collapsed and translated into the inter-fitted, compressed segment configuration. Also, concentrated forces imparted by the edges of segments on the debris as well as forces imparted by the vertical surfaces of segments on debris 7 that becomes trapped between adjacent segments as the wound interface layer 10 collapses assist in the debridement of debris 7 at the tissue site 5.

According to various embodiments, the density of the material used to form the wound interface layer 10 may be varied as desired to control the degree by which the wound interface layer 10 may be vibrated, oscillated and/or otherwise moved relative to the tissue site 5 in response to the vibrational energy and/or oscillatory movement that is imparted onto the wound interface layer 10 by the active layer 40. Similarly, in embodiments in which the wound interface layer 10 is formed with a plurality of through-holes 13, the thickness of the walls separating adjacent through-holes 13 and/or the size of the openings defined by through-holes 13 may also be varied to control the degree by which the wound interface layer 10 may be vibrated, oscillated and/or otherwise moved relative to the tissue site 5 in response to the vibrational energy and/or oscillatory movement that is imparted onto the wound interface layer 10 by the active layer 40.

ii. Active Layer

Active layer 40 is configured to intentionally translate the wound dressing 100 in a horizontal and/or vertical direction relative to the tissue site 5 such that unhealthy tissue or other debris 7 may be debrided from the tissue site 5. In various embodiments, upon activation of the drive unit 70, the active layer 40 is adapted to oscillate/rotate (e.g. concentrically, eccentrically, orbitally, etc.) and/or vibrate to achieve a desired translation of the wound interface layer 10.

As illustrated in FIGS. 2 and 3, the active layer 40 generally comprises one or more transmission layers 45 extending radially outwards from a central post 47 that is operably connected to a drive unit 70. Upon activation of the drive unit 70, vibration and/or oscillation imparted by the drive unit 70 to the central post 47 is further transmitted to some or all of the transmission layers 45 via the central post 47, with the resultant vibration and/or oscillation of the one or more transmission layers 45 being transferred to the wound interface layer 10 to effectuate mechanical debridement of debris 7 at the tissue site 5.

In embodiments in which the active layer 40 is configured to be oscillated/rotated by the drive unit 70, such as, e.g. illustrated in FIG. 4A, the activation of the active layer 40 may result in rotation of the transmission layer 45 about the central post 47 while the central post 47 remains stationary relative to the tissue site 5. In other such embodiments, activation of the active layer 40 may result in rotational movement of the transmission layer 45 and central post 47 relative to the tissue site 5 while maintaining the transmission layer 45 stationary relative to the central post 47. In yet other embodiments, activation of the active layer 40 may result in orbital movement of the transmission layer 45 and central post 47, with the transmission layer 45 rotating relative to the central post 47 while both the transmission layer 45 and the central post 47 are rotated relative to the tissue site 5.

In any such embodiments in which oscillatory/rotational movement is used to drive the active layer 40, it is to be understood that the transmission layer(s) 45 and/or central post 47 may be activated to achieve any desired degree of rotation. According to various embodiments, the transmission layer 45 and/or central post 47 may be activated by the drive unit 70 to rotate by less than approximately 30 degrees of rotation, and more preferably less than approximately 5 degrees. According to some embodiments, this small back and forth rotational movement may be effectuated via high frequency vibrations imparted by the drive unit 70.

a. Transmission Layer

The transmission layer 45 defining the active layer 40 may be formed according to any number of embodiments, with the transmission layer 45 being adapted such that the selection of shape, size, configuration and/or materials used to form the transmission layer 45 may allow a user control the rate and degree of movement of the wound interface layer 10 relative to the tissue site 5 during operation of the wound debridement system 1. As illustrated in FIGS. 3B and 3C, according to various embodiments, the active layer 40 may comprise a single transmission layer 45, while in other embodiments, such as, e.g. illustrated in FIGS. 2, 3A and 3D, the active layer 40 may comprise a plurality of vertically spaced transmission layers 45.

In general, as compared to, e.g. applying vibrational/oscillatory energy along a top of the drape layer 20, which results in much of the vibrational/oscillatory energy being directed to the skin around the tissue site 5, the transmission layer 45 is configured to distribute/transmit the vibrations/oscillations that are delivered thereto from the drive unit 70 directly to the wound dressing 100, such that vibrations/oscillations transmitted via the transmission layer 45 are more directly applied to tissue site 5 than those applied along the top of the drape layer 20.

According to various embodiments, the degree of vibrational energy and/or rotational movement that is transferred to the wound interface layer 10 by the active layer 40 may be controlled via the selection of the rigidity of the material(s) used for the transmission layer(s) 45, with more rigid materials being capable of transferring a greater amount of energy and/or movement to the wound interface layer 10 than less rigid materials. As such, in embodiments in which more aggressive wound debridement is desired, the transmission layer(s) 45 may be formed from a more rigid material than would be used to form the transmission layer(s) 45 of a wound debridement system 1 intended to be used in a gentler debridement procedure. In various embodiments, the materials used to form the transmission layer(s) 45 may comprise any number of materials, including e.g. various mid-durometer polymers.

As shown in FIGS. 2 and 3, the one or more transmission layers 45 are positioned about and extend radially outwards from a central post 47 to which the drive unit 70 is attached. Upon activation of the drive unit 70, the vibrational energy and/or oscillatory movement generated by the drive unit 70 is transmitted through the central post 47 to drive the transmission layer(s) 45. According to various embodiments, such as, e.g. shown in FIGS. 2, and 3B-3D, the transmission layer(s) 45 may be fixedly attached to the central post 47, such that any vibration or movement of the central post 47 is directly transmitted to the transmission layer(s) 45. In other embodiments, such as, e.g. shown in FIG. 3A, the transmission layer(s) 45 may be movably attached to the central post 47 (via e.g. an attachment of the transmission layer 45 to a collar 48 that rotatably surrounds the central post 47), such that the vibrational energy and/or oscillatory movement of the central post 47 may be selectively transmitted to the transmission layer(s) 45.

In some embodiments, the transmission layer 45 may comprise a generally solid, continuous, and planar structure that extends radially outwards from the central post 47. In other embodiments, the transmission layer 45 may be defined by a non-continuous, planar structure that extends partially or entirely about the central post 47 and which is formed of one or more rigid or semi-rigid arm members 43. In various embodiments, the outermost dimensions of the transmission layer 45 may be customizable (e.g. the transmission layer 45 may be trimmable) such that the outermost dimensions of the transmission layer 45 may be adapted to the size and shape of the tissue site 5.

In embodiments in which the transmission layer(s) 45 is comprised of one or more rigid or semi-rigid arm members 43, the arm members 43 may be formed as discrete elements, with each individual arm member 43 being independently attached to the central post 47, such as e.g. illustrated in FIGS. 2 and 3A. In other embodiments, such as, e.g. illustrated in FIGS. 3B-3D, the transmission layer(s) 45 may be defined by a structure formed of a plurality of monolithically or integrally interconnected arm members 43. In such embodiments, the pattern, arrangement and spacing of the arm members 43 may advantageously be varied and selected as desired so as to provide for the desired vibration and/or oscillation of the active layer 40 upon activation of the drive unit 70. In such embodiments, the arm members 43 may form an interconnected structure defined by any number of uniform or non-uniform patterns and designs, such as, e.g. a spiderweb, target-shaped, grid, spiral, hub-and-spoke, etc.

As described below, in various embodiments, the drive unit 70 may be adapted to generate varying levels of vibrational energy and/or rotational movement, such that varying degrees of movement of the wound interface layer 10 relative to the tissue site 5 may be achieved. In other embodiments, the selection of materials used to form the transmission layer 45 (such as, e.g. forming differing transmission layers 45 from materials having differing rigidities) may also be used to achieve varying degrees of movement of the wound interface layer 10 relative to the tissue site 5.

In some embodiments, additional control over the degree of movement of the wound interface layer 10 relative to the tissue site 10 may be provided by operatively isolating one or more transmission layers 45 from each other, such that vibration and/or oscillation of one or more transmission layers 45 may be induced via vibrational energy and/or rotational movement transferred from the central post 47 without automatically inducing vibration and/or oscillation in other transmission layers 45. In such embodiments, the selective activation of certain operatively isolated, individual transmission layers 45 may provide additional control over the degree and/or extent of vibration and/or oscillation that the wound interface layer 10 is subject to.

iii. Film Layer

As noted above, in various embodiments, the transmission layer(s) 45 of active layer 40 may be embedded within the wound interface layer 10 and/or the absorbent layer 30. However, in embodiments in which the transmission layer(s) 45 of active layer 40 are provided as a discrete, non-embedded layers, wound dressing 100 may optionally include a film layer (not shown) to which the transmission layer(s) 45 of the active layer 40 may be mounted, laminated, attached or otherwise interconnected to, with the film layer also being used as the basis by which the transmission layer(s) 45 may be affixed to the wound interface layer 10 and/or absorbent layer 30. Alternatively, in some embodiments in which the active layer 40 is not embedded, the film layer may be omitted, with the transmission layer(s) 45 of the active layer 40 being attached directly to the wound interface layer 10 and/or absorbent layer 30.

The size and shape of the film layer may be varied as desired. In various embodiments, the outer periphery of the film layer may be shaped and sized to generally correspond to, or optionally be smaller than, the outer periphery of the wound interface layer 10.

The film layer may be adapted to elastically deform upon application of a stretching force to the wound dressing 100. For example, in some embodiments, the film layer may be designed to elastically stretch when a stretching force is applied and elastically recover when the stretching force is removed, such as, e.g. may occur as a result of the vibration and/or rotation of the transmission layer(s) 45 that is supported by film layer. In other words, film layer may be configured to exhibit substantially elastic deformation and recovery.

Film layer may be a thin layer made of any number of elastic materials. For example, film layer may be a polyurethane film, a polyethylene film, or other thin elastic. In some embodiments, film layer may be substantially impermeable to liquid and substantially permeable to moisture vapor.

In embodiments in which the wound debridement system 1 will be used with additional therapeutic treatments, such as, e.g. NPWT or instillation therapy, film layer may optionally include one or more fenestrations adapted to allow for the transfer of fluids and pressure to/from the wound interface layer 10. The fenestrations may also be adapted to reduce the amount of force required to stretch film layer.

In some embodiments, film layer may comprise an upper film and a lower film that encapsulate the transmission layer(s) 45 of the active layer 40. In some such embodiments, one or both of the upper film and the lower film may include fenestrations.

iv. Absorbent Layer

An absorbent layer 30 may optionally be coupled to the active layer 40 opposite the wound interface layer 10, such that the active layer 40 is encapsulated between the absorbent layer 30 and the wound interface layer 10. The absorbent layer 30 may act as a manifold that is adapted to collect and/or distribute fluid and/or pressure across a tissue site 5. For example, the absorbent layer 30 may be adapted to receive and distribute negative pressure across a tissue site 5 to which the wound dressing 100 is applied, allowing for the wicking of fluid (e.g. exudate) from the tissue site 5 and providing a distributed compressive force along the tissue site 5. As another example, the absorbent layer 30 may be used to facilitate the delivery of fluid across a tissue site 5.

In embodiments incorporating an absorbent layer 30, the size and shape of the absorbent layer 30 may be varied as desired. In various embodiments, the outer periphery of the absorbent layer 30 may be shaped and sized to generally correspond to, or optionally be smaller than, the outer periphery of the wound interface layer 10. As illustrated in FIG. 2, the absorbent layer 30 may include a port opening 35 through which the central post 47 of the active layer 40 and/or the drive shaft 73 of the drive unit 70 extends.

Any material or combination of materials might be used for the absorbent layer 30. In some embodiments, the absorbent layer 30 may comprise a porous and permeable foam layer, with the absorbent layer 30 being formed from a reticulated, open-cell polyurethane or polyether foam that allows good permeability of wound fluids while under a reduced pressure. In one non-limiting example, the absorbent layer 30 may be an open-cell, reticulated polyurethane foam such as GranuFoam® dressing available from Kinetic Concepts, Inc. of San Antonio, Tex. In other embodiments the absorbent layer 30 may be an open-cell, reticulated polyurethane foam such as a V.A.C. VeraFlo® foam, also available from Kinetic Concepts, Inc., of San Antonio, Tex. In yet other embodiments, the absorbent layer 30 may be formed of un-reticulated open-cell foam.

Support Layer

In some embodiments, the wound debridement system 1 may further comprise a support layer 50 positionable over the wound dressing 100 that is configured to maintain the wound dressing 100 in place during operation of the wound debridement system 1, while also preventing the wound dressing 100 from sticking to the drape layer 20. According to one embodiment, support layer 50 may be a support layer such as that shown and described in U.S. patent application Ser. No. 16/678,450, the complete disclosure of which is incorporated herein by reference in its entirety.

The inclusion of such a support layer 50 may be particularly advantageous in embodiments in which the wound debridement system 1 is used to treat tissue sites 5 located on areas of the body that encounter a wide range of motion and frequent movement, such as, e.g. elbow, knee cap, etc.

In general, the support layer 50 is configured to dampen the vibration and/or oscillation of the wound dressing 100 to prevent the wound dressing 100 from being displaced relative the treatment tissue site 5 as a result of the vibratory and/or oscillatory forces imparted onto the wound dressing 100 by the drive unit 70 and to maintain a close contact between the wound interface layer and the tissue site 5 during treatment. In such a manner, the support layer 50 may be adapted to ensure that the movement of the wound interface layer 10 is localized to movement within an area corresponding to the tissue site 5 such that debridement at the tissue site 5 may be achieved. As illustrated in FIG. 2, the support layer 50 may include a port opening 55 through which the central post 47 of the active layer 40 and/or the driving shaft 73 of the drive unit 70 extends.

In some embodiments, support layer 50 may comprise a semi-rigid and porous material, such as a rubber or plastic material such as polyurethane. In other embodiments, support layer 50 may comprise a substantially rigid material, which may be non-porous and non-permeable. In still other embodiments, support layer 50 may comprise areas of differing rigidity, such that support layer 50 is configured to match the anatomy of a particular tissue site 5. Support layer 50 may also have areas of differing thickness to further match the contours of a particular tissue site 5.

Advantageously, support layer 50 may be formed by a process such as three-dimensionally printing or casting that allows for the customization of the support layer 50 to a particular tissue site 5. The three-dimensional printing or casting of the support layer 50 allows for the creation of a wound dressing 100 contoured to the unique shape and size of the tissue site 5, such that the wound debridement system 1 may be better adhered to the unique tissue site 5 that is to be treated. Additionally, support layer 50 may be printed or casted to have areas of varying thickness or rigidity in order to better match the contours of the tissue site 5.

In some embodiments, support layer 50 includes an antimicrobial agent or other active agents to promote effective wound healing and/or which may interact with the wound bed to breakdown wound exudate. Non-limiting examples of such active materials may include antimicrobial silver, silver oxidized regenerated cellulose (ORC) (e.g., approximately 25 wt % ionically bound silver), polyhexamethylene biguanide (PHMB), nonsteroidal ant-inflammatory drugs such as acetaminophen, steroids, anti-inflammatory cytokines, anesthetics, antimicrobial agents such as penicillin or streptomycin, antiseptics such as chlorhexidine, growth factors such as fibroblast growth factor (FGF), a platelet derived growth factor (PDGF), or an epidermal growth factor (EGF), and other therapeutic agents, individually or in any combination. If present, such active materials may typically be included at any effective level that show therapeutic efficacy, while preferably not being at such a high level as to significantly counteract any critical or desired physical, chemical, or biological property of the dressing. Depending upon the therapeutic goal, any active material may be loaded at a level of from about 10 wppm to about 10 wt % of the layer in which it is present, for example, from about 50 wppm to about 5 wt % or from about 100 wppm to about 1 wt %. The active material may be contained within a thin film on second side 120 of support layer 50 or may be distributed within support layer 50.

In embodiments in which the wound dressing 100 does not include an absorbent layer 30 and the wound interface layer 10 is formed with a plurality of through-holes 13, the support layer 50 may comprise one or more surface disruptors (not shown) distributed along a lower surface of support layer 50 to facilitate in the disruption and fragmentation of debris 7 that becomes trapped within the through-holes 13. Non-limiting examples of surface disruptors include, e.g. projections, protrusions, texture, abraders, microspikes, etc.

Drape Layer

A drape layer 20 adapted to seal to a patient's skin may advantageously be provided to position and maintain the active debridement wound dressing 100 about the desired treatment tissue site 5. An attachment device, such as e.g. an adhesively coated margin 23, as illustrated e.g. in FIG. 1 may be used to attach the drape layer 20 to a desired location along the patient's skin. In various embodiments, the drape layer 20 may provide a bacterial barrier and protection from physical trauma, and may be permeable to water vapor but impermeable to liquid. In the embodiment shown in FIG. 1, drape layer 20 may include a port opening 25 through which the central post 47 and/or the driving shaft 73 of the drive unit 70 extends.

Drape layer 20 may be formed from any number of materials, such as, e.g. polyurethane film. In some embodiments, the drape layer 20 may be adapted to provide a fluid-tight seal with the patient's skin surrounding the tissue site 5 that is to be treated. In such embodiments, the drape layer 20 may be constructed from a material adapted to reduce evaporative losses and provide and maintain a fluid seal. As non-limiting examples, the drape layer 20 may be formed from materials that include a silicone, 3M Tegaderm® drape material, acrylic drape material such as one available from Avery, or an incise drape material.

Attachment Port

As illustrated in FIGS. 1 and 2, in various embodiments, an attachment port 90 may be provided on the drape layer 20 or the support layer 50. The attachment port 90 may advantageously provide a fluid tight seal that allows for the central post 47 to be operably attached to a driving shaft 73 of the drive unit 70 while maintaining the sterility of the interior of the wound debridement system 1. In some embodiments, the attachment port 90 may provide for such a sterile connection via the inclusion of a check valve. One non-limiting example of an attachment port 90 that may be used is a SENSA-T.R.A.C.™ port as available from Kinetic Concepts, Inc. (KCI) of San Antonio, Tex.

Referring to FIG. 4B, in some embodiments in which the drive unit 70 is configured to generate a vibrational energy and in which the attachment port 90 is attached about an upper surface of the support layer 50 or drape layer 20, the attachment port 90 may optionally also be configured to transfer vibrational energy received from the drive unit 70. Such embodiments may be advantageous, e.g., where the wound debridement system 1 is used in conjunction with a NPWT treatment system in which debris is removed by the NPWT system via a conduit that passes through the attachment port 90. In particular, the vibrational energy imparted by the attachment port 90 may be configured to assist in breaking up and/or solubilizing debris passing through the conduit, such that the vibrational energy imparted by the attachment port 90 may be used to prevent blockage of the conduit.

Drive Unit

The drive unit 70 of the wound debridement system 1 is configured to transmit vibrational energy and/or rotational movement to the active layer 40 to effectuate movement of the wound interface layer 10 relative to the tissue site 5. As will be understood, the drive unit 70 may incorporate any known type of transducer, such as, e.g. a flat planar piezoelectric or magnetostrictive transducer capable of transforming electrical signals into longitudinal or transverse vibrations and/or rotational movement. According to various embodiments, the drive unit 70 may be configured to operate at frequencies within a range of between approximately 2 Hz to approximately 400 Hz, and more specifically frequencies within a range of between approximately 20 Hz to approximately 200 Hz.

In some embodiments, e.g. as illustrated in FIGS. 4A and 4B, the drive unit 70 may be provided external to the drape layer 20, support layer 50, and/or wound dressing 100, with a drive shaft 73 of the drive unit 70 being operably attached to the central post 47 of the active layer 40 through an attachment port 90. In other embodiments (not shown), the drive unit 70 may be located within the drape layer 20 and/or support layer 50, such that the wound debridement system 1 defines a self-contained unit that may be positioned at the desired tissue site 5.

Control Unit

The activation of the active layer 40 by the drive unit 70 may be based upon signals received from an optionally included control unit 80. In some embodiments, the control unit 80 and drive unit 70 may be formed as a single unit, while in other embodiments the drive unit 70 and control unit 80 may be provided separately. The communication between the control unit 80 and the drive unit may be accomplished using any number of known communication methods, including wireless communication.

As will be understood, in addition to simply starting and stopping the movement of the active layer 40, the control unit 80 may also be adapted to allow for the adjustment and variation of the movement of the active layer 40. The control unit 80 may be adapted to vary the degree of vibrational energy and/or rotational movement generated by the drive unit 70 based on any number of factors including, but not limited to: the tissue site 5 being treated (such as, but not limited to bone tissue, adipose tissue, muscle tissue, neural tissue, dermal tissue, vascular tissue, connective tissue, cartilage, tendons, or ligaments, chronic, acute, traumatic, subacute, and dehisced wounds, partial-thickness burns, ulcers, flaps, grafts, etc.); the type of debris 7 being debrided (such as, but not limited to necrotic tissue, eschar, impaired tissue, other sources of infection, exudate, slough including hyperkeratosis, pus, foreign bodies, biofilm, or other types of bioburden, etc.); the thickness, consistency, color and/or moisture levels of the debris 7; the desired relative amount of movement of the wound interface layer 10 relative to the tissue site 5; etc.

Standalone Use and Use With Other Treatment Systems

In various embodiments, wound debridement system 1 may be used as a standalone therapy device, with drive unit 70 and optional control unit 80 being provided solely for the operation of the wound debridement system 1. However, as noted previously, in other embodiments it may be possible to utilize the wound debridement system 1 in conjunction with one or more additional therapeutic treatment systems configured to provide a desired therapeutic treatment to the tissue site 5 in addition to the debris 7 debridement provided by the wound debridement system 1.

In embodiments in which the wound debridement system 1 is used in conjunction with another therapeutic treatment system, one or more of the components of the wound debridement system 1 may optionally comprise one or more elements of the additional therapeutic treatment system or vice versa. For example, in embodiments in which the wound debridement system 1 is used in conjunction with an additional therapeutic treatment system used to remove and/or deliver fluids to the tissue site (such as, e.g. a NPWT and/or instillation treatment system) the central post 47 may optionally be modified to include a channel through which the fluids of the adjunct treatments may be removed and/or delivered.

In various embodiments, the additional therapeutic treatment system that the wound debridement system 1 is used in conjunction with may be a NPWT system. The use of the wound debridement system 1 with the NPWT system may improve the functioning of both systems, as the debridement of the debris 7 at the tissue site 5 may improve the efficacy of the NPWT treatment, while the negative pressure applied by the NPWT system may advantageously assist in removing the debris 7 that has been loosened and removed from the tissue site 5 by the wound debridement system 1.

In some embodiments, the wound debridement system 1 may be used in conjunction with an instillation therapy system. In such embodiments, a NPWT system may also optionally be included. The instillation therapy system may assist in the hydration and flushing of the tissue site 5, which may facilitate the debridement of the debris 7 by the wound debridement system 1. In turn, the wound debridement system 1 may allow for greater control of the instillation therapy system.

More specifically, in some embodiments, the active layer 40 may be actuated by the drive unit 70 during the instillation fill, soak and removal phases of instillation therapy. During the fill phase, the actuation of the active layer 40 may encourage a thorough and uniform distribution of the instillation fluid at the tissue site 5 by the wound interface layer 10. During the soak phase, the hydrating effect of the instillation fluid at the tissue site 5 may increase the debridement efficiency of wound interface layer 10. Additionally, in some embodiments, the instillation fluid may optionally contain a topical solution that may assist in reducing patient discomfort during the debridement process. Finally, the flushing and fluid removal phase of the instillation therapy may encourage and assist in the removal of debrided debris 7 from the tissue site 5.

In some embodiments, the wound debridement system 1 may be used in conjunction with (either before, during or after) existing tissue removal and debridement systems and methods. For example, the wound debridement system 1 may be used prior to enzymatic debridement to soften the debris 7. In another example, an existing mechanical debridement technique or method may be used to remove a portion of the debris 7 at the tissue site 5, and the wound debridement system 1 may then be used to remove the remaining debris 7 while reducing the risk of trauma to the tissue site 5.

Although not shown, in some embodiments in which the wound debridement system 1 is used in conjunction with a NPWT and/or instillation therapy device, one or more of the transmission layers 45 forming the active layer 40 may optionally be formed as a hollow structure having one or more ports that are in fluid communication with a source of negative pressure and/or fluid that is provided via a fluid channel formed through the central post 47. In such a manner, the active layer 40 may optionally be used to both drive the wound interface layer 10 to debride the tissue site 5 and to assist in the distribute/remove fluids to/from the tissue site 5.

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

We claim:

1. An active debridement wound dressing comprising:
   a wound interface layer configured to contact a wound and mechanically debride the wound when the wound interface layer moves relative to the wound; and
   an active layer coupled to the wound interface layer and comprising a transmission layer extending radially outwards relative to a central post, the transmission layer being configured to vibrate in response to a vibrational energy transmitted to the transmission layer by the central post so as to move the wound interface layer relative to the wound and mechanically debride the wound.

2. The active debridement wound dressing of claim 1, wherein the transmission layer is formed from a plurality of arm members.

3. The active debridement wound dressing of claim 2, wherein the plurality of arm members form an interconnected, interrupted planar structure.

4. The active debridement wound dressing of claim 1, wherein the wound interface layer is formed from a foam material.

5. The active debridement wound dressing of claim 4, wherein a plurality of through-holes extend through the wound interface layer, the plurality of through-holes being distinct from pores which define the foam material from which the wound interface layer is formed.

6. The active debridement wound dressing of claim 4, further comprising an absorbent layer, the absorbent layer being distinct and separate from the wound interface layer.

7. The active debridement wound dressing of claim 6, wherein the transmission layer is positioned on top of a top surface of the wound interface layer and below a lower surface of the absorbent layer.

8. The active debridement wound dressing of claim 1, wherein the transmission layer is at least partially embedded within the wound interface layer.

9. The active debridement wound dressing of claim 1, wherein the active layer comprises a plurality of vertically spaced transmission layers.

10. The active debridement wound dressing of claim 1, further comprising a drive unit configured to generate the vibrational energy operably attached to the central post.

11. The active debridement wound dressing of claim 1, further comprising a semi-rigid support layer positioned between a drape layer and the wound dressing, the support layer configured to prevent the wound dressing from sticking to the drape layer and to prevent the wound dressing from being unintentionally displaced from a desired treatment area in response to a vibrational energy being applied to the wound dressing.

12. An active debridement wound dressing comprising:
    a wound interface layer configured to contact a wound and mechanically debride the wound when the wound interface layer moves relative to the wound; and
    an active layer coupled to the wound interface layer and comprising a transmission layer extending radially outwards relative to a central post, the transmission layer being configured to rotate when activated so as to move the wound interface layer relative to the wound and mechanically debride the wound.

13. The active debridement wound dressing of claim 12, wherein the transmission layer is formed from a plurality of arm members.

14. The active debridement wound dressing of claim 12, wherein the wound interface layer is formed from a foam material.

15. The active debridement wound dressing of claim 12, wherein the transmission layer is at least partially embedded within the wound interface layer.

16. The active debridement wound dressing of claim 12, wherein the active layer comprises a plurality of vertically spaced transmission layers.

17. The active debridement wound dressing of claim 12, wherein the transmission layer is movably attached to the central post, such that the transmission layer may be rotated relative to the central post.

18. The active debridement wound dressing of claim 12, wherein the transmission layer is configured to rotate in an orbital motion.

19. A method of debriding a wound comprising:
providing a dressing including a wound interface layer configured to contact a wound and mechanically debride the wound when the wound interface layer moves relative to the wound;
providing an active layer coupled to the wound interface layer, the active layer comprising a transmission layer configured to transmit vibration or oscillation across the wound dressing;
transmitting at least one of a vibrational or an oscillatory motion to the wound interface layer via the transmission layer; and
rotating the transmission layer relative to a central post in response to the transmitted vibrational or oscillatory motion.

20. The method of claim 19, further comprising providing a therapy unit separate from the wound dressing, the therapy unit configured to generate and apply at least one of the vibrational or the oscillatory motion to the active layer.

* * * * *